United States Patent [19]

Matsumura

[11] 4,251,139
[45] Feb. 17, 1981

[54] EYE EXAMINING INSTRUMENT

[75] Inventor: Isao Matsumura, Yokosuka, Japan

[73] Assignee: Canon Kabushiki Kaisha, Tokyo, Japan

[21] Appl. No.: 906,094

[22] Filed: May 15, 1978

[30] Foreign Application Priority Data

May 20, 1977 [JP] Japan ................................ 52-58239

[51] Int. Cl.³ .......................... A61B 3/10; A61B 3/14; G03B 29/00
[52] U.S. Cl. ......................................... 351/7; 351/13; 351/6; 354/62
[58] Field of Search ............... 356/153, 399, 4; 351/1, 351/6, 13, 16, 9, 7; 350/2; 354/62

[56] References Cited

U.S. PATENT DOCUMENTS

| | | | |
|---|---|---|---|
| 3,724,923 | 4/1973 | Cornsweet et al. | 351/7 |
| 3,780,979 | 12/1973 | de Guillebon | 351/16 |
| 3,864,030 | 2/1975 | Cornsweet | 351/7 |
| 3,915,564 | 9/1974 | Urban | 351/7 |

Primary Examiner—John K. Corbin
Assistant Examiner—Rodney B. Bovernick
Attorney, Agent, or Firm—Fitzpatrick, Cella, Harper & Scinto

[57] ABSTRACT

Eye examining instrument is improved with respect to its spacing and alignment relative to a human eye to be examined is disclosed. For the purpose of the spacing and alignment, a non-imaging beam coming from a mark is directed to the cornea of the eye through an objective lens of the eye examining instrument. The beam is reflected upon the cornea surface in a manner of specular reflection and then imaged through the objective lens. The image of the mark is detected. At the position at which the image of mark is formed there is disposed, for transmitting the mark image to a television camera of the eye examining instrument, an input surface of a relay lens group or an input surface of a bundle of fibers or a photoelectric cell with its light receiving surface being partly covered with a masking plate.

9 Claims, 11 Drawing Figures

EYE EXAMINING INSTRUMENT

BACKGROUND OF THE INVENTION

1. Field of the Invention

The present invention relates to an eye refractometer or an examining and testing instrument such as retinoscope and eye fundus camera.

2. Description of the Prior Art

To effect a precise measurement or observation, and also to obtain a good photographic picture, it is essentially of importance to correctly align and space the instrument with and from the eye. If alignment is incorrectly made, then there will be caused an error of measurement. In the case of a fundus camera, a portion of the picture taking light may be dispersed by the iris of the eye due to the incorrect alignment. Also, incorrect spacing causes various problems. Usually, spacing is made by structurally predetermining the distance between the objective lens of the instrument and a holder on which the face of the examinee is unmovably held. The adjustment of the distance between the objective lens and the eye, that is generally called the working distance, is very important in particular when a fundus camera is used. If the operator fails to accurately adjust the working distance, a portion of light illuminating the fundus is reflected by the cornea of the eye and the reflected light adversely enters into the picture taking light. As a result, a flare is produced in the picture image. When a correct spacing is achieved, it will also contribute to a substantial improvement of measuring accuracy of an instrument such as a refractometer.

U.S. Pat. No. 3,871,772 describes a positioning system of an eye examining instrument. According to the teaching of this prior art, the anterior part of eye to be examined is uniformly illuminated with infrared light and the eye anterior is observed by employing an aiming device supported on the body of the apparatus. Alignment and spacing are adjusted by aligning the center of the aiming plate with the center of the image of the eye pupil. However, this prior art system has some drawbacks. The whole of the eye anterior becomes visible in the visual field of the aiming device. Furthermore, the resolving power of the image is substantially reduced due to the presence of an image intensifier mounted in the aiming device. Therefore, it is impossible or difficult to judge whether or not the image of the eye anterior is clear and sharp. For this reason, the adjustment of both alignment and spacing must be carried out in accordance with the deviation of the center of the image of the pupil from the center of the aiming plate. Alignment and spacing can not be carried out independently of each other.

For a conventional fundus camera, alignment is usually carried out in the following manner:

Initially, the camera body is moved in the direction away from the eye so as to focus the objective lens on the pupil of eye. Then, the position of the camera is adjusted in vertical and horizontal directions until the center of the view field in the view finder coincides with the center of the pupil. After this adjustment, the camera is moved back to the first position.

Thus, alignment is relatively easy to carry out, but, the above described procedure is not applicable for spacing. It is, therefore, very difficult to carry out spacing independently of alignment.

SUMMARY OF THE INVENTION

Accordingly, it is the primary object of the invention to make it possible to correctly adjust the spacing between an eye examining instrument and a human eye to be examined.

The present invention is based on the finding that the cornea of the human eye possesses a property similar to that of a convex mirror. According to the invention, a beam which specular-reflects upon a cornea is projected toward the cornea of an eye to be examined. Thus, it is possible to detect such beam which contains no information of the cornea.

Other objects, features and advantages of the invention will appear more fully from the following description taken in connection with the accompanying drawing.

DESCRIPTION OF THE PREFERRED EMBODIMENTS

Figure 1:
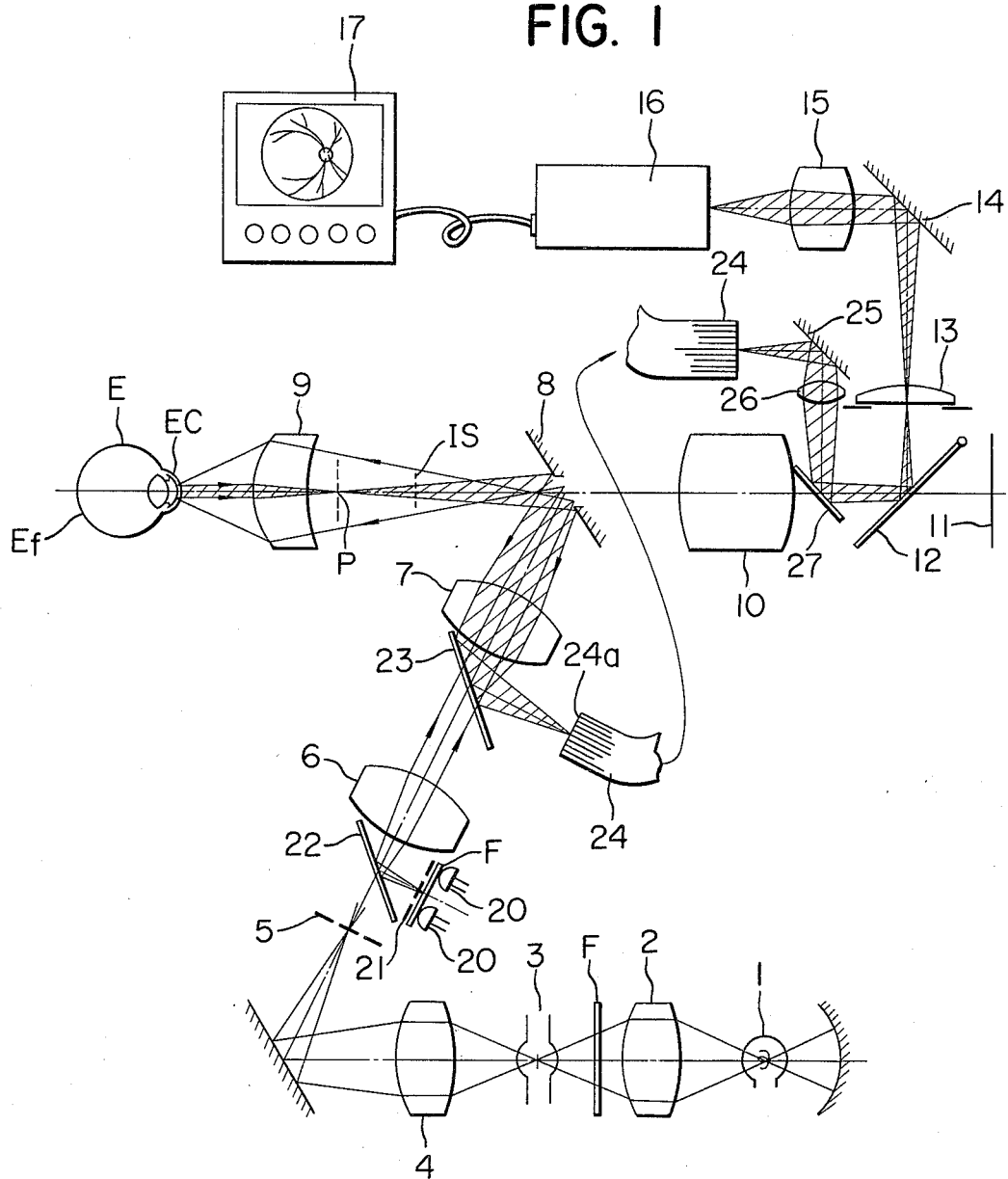
FIG. 1 schematically shows an embodiment of the present invention.
Figure 2:
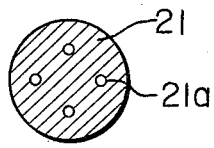
FIG. 2 is a plan of the indication plate used in the embodiment.

Referring first to FIG. 1 there is shown an embodiment of the invention applied to a fundus camera.

In the drawing of FIG. 1, E is an eye to be tested, Ec is the cornea and Ef is the fundus of the eye. 1 is a tungsten lamp, 2 is a condenser lens, F is a filter which transmits only infrared and near infrared rays, 3 is a strobo tube, 4 is a condenser lens and 5 is a slit plate with a ring slit. The lamp 1 and the strobo tube 3 are conjugate relative to the condenser lens 4, and the image of the lamp 1 and the strobo tube are conjugated with the slit plate 5 with respect to the condenser lens 4. The reference numerals 6 and 7 designate relay lenses, 8 is a bored mirror with an opening and 9 is an objective lens. The image of the slit plate 5 is formed at first on the bored mirror 8 under the action of the relay lenses 6 and 7 and is thereafter formed again at a position in the vicinity of the pupil of the eye through the objective lens 9. The above mentioned elements 1 through 9 constitute an illumination system.

Designated by 10 is an imaging lens group which is disposed behind the objective lens 9 with its optical axis aligned with the optical axis of the latter. The reference numeral 11 designates a film. The objective lens 9, the stop opening of the bored mirror 8 the imaging lens group 10 and the film 11 together constitute a picture taking system (photographing system). The objective lens 9 is focused on the fundus Ef and the imaging lens group 10 images the image of the fundus formed by the objective lens 9 on the film 11. A separate stop for the photographing system may be provided in the vicinity of the opening of the bored mirror 8.

Designated by 12 is a jump-up mirror which can be brought into its retracted position outside of the effective beam when a picture of the fundus is taken. During the observation, the jump-up mirror is positioned obliquely in the light path of the beam. 13 is a field lens which is disposed conjugated with the film 11 with respect to the mirror 12. 14 is a mirror for changing-over the light path and 15 is a converging lens for picking up an image. 16 is a vidicon which is sensitive to light of infrared range. Designated by 17 is a Braun tube used for displaying a signal of a pick-up tube such as vidicon 16 after the signal has been processed in a processing circuit (not shown). The above mentioned elements 12 through 17 and the objective lens 9 and the imaging lens group 10 together constitute an observation system.

The objective lens 9 is common to the illumination system, the photographing system and the observation system.

Now, an indication projecting system is described in detail.

Designated by 20 is a set of luminescence diodes and F is a filter for infrared rays. 21 is an indication plate having therein a plural number of holes 21a and 21b. The luminescence diodes are disposed behind these holes (indication) provided in the indication plate respectively. 22 and 23 are semitransparent mirrors (half mirrors). Light rays emerging from the holes of the indication plate are reflected by the half mirror 22 toward the relay lens 6. After passing through the relay lenses 6 and 7 and then being reflected by the mirror surface of the bored mirror 8, the light rays are once concentrated. The concentrated light rays then diverge to form a divergent beam running toward the objective lengs 9 by which the divergent beam is converged to form a convergent beam. The convergent beam is directed to the cornea Ec and reflected upon the surface of the cornea located at a predetermined position. The beam thus reflected again enters the objective lens 9 in the opposite direction to that in which the beam previously entered the lens 9. Passing through the objective lens 9, the reflected beam is focused in the plane of P lying between the objective lens and the imaging plane of the objective lens 9.

Light rays leaving the plane P for the bored mirror 8 are reflected by the latter, converged by the relay lens 7 and reflected by the half mirror 23. At the position where the light rays reflected by the half mirror 23 are focused, there is disposed the input end 24a of a bundle of optical fibers 24 adapted for image transmission. As will be understood from the foregoing, the indication plate 21 and the input end 24a of the fiber bundle are in a conjugated relation with respect to half mirror 22, relay lenses 6 and 7, the mirror surface of bored mirror 8, objective lens 9, cornea Ec, objective lens 9, the surface of bored mirror 8, relay lens 7 and half mirror 23.

Designated by 25 is a mirror for changing-over the light path, 26 is a relay lens and 27 is a half mirror. The half mirror 27 is retracted from the light path of the effective beam when a picture of the fundus is taken. Here, it should be noted that the output end of the bundle of optical fibers and the image pick-up surface of the vidicon are conjugated with respect to the elements of 25, 26, 27, 12, 13, 14 and 15.

With the fundus camera of the above described arrangement, a picture of the fundus is taken according to the non-mydriatic method employing a combination of infrared beam and a vidicon for infrared light. However, the non-mydriatic method may be also carried out by employing a super high sensitive pick-up tube provided with an image intensifier positioned directly before the vidicon while decreasing the intensity of light of the lamp 1 and luminescence diodes 20 to the extent that no contraction of the pupil of the eye may be caused.

The manner of operation of the above described embodiment is as follows:

When the lamp 1 is put on and also the vidicon 16 and the Braun tube 17 are brought into operation, an image of the fundus is displayed on the screen of the Braun tube. In addition, by turning the luminescence diodes 20 on, four light spots appear on the screen together with the image of the fundus. More particularly, a beam of light emitted from the light source is converged by the condenser lens 2 and from the beam only the infrared and near infrared component is taken up through the filter F. The beam once converged by the condenser lens 2 now diverges and then it is again converged by the condenser lens 4 so as to illuminate the slit plate 5. The beam emerging from the ring slit of the plate 5 is converged on the bored mirror 8 through the relay lenses 6 and 7. The converged beam becomes divergent from the mirror and enters the objective lens 9. The objective lens 9 converges the beam on a plane close to the pupil of the eye so as to illuminate the fundus Ef.

The beam reflected upon the fundus Ef in a manner of scatter-reflection leaves the eye for the objective lens 9 by which the beam is imaged on the imaging plate IS. Thereafter, the beam passes through the stop of the bored mirror 8 and it is again imaged on the field lens 13 through the imaging lens group 10 and the jump-up mirror 12. Finally, the beam is imaged on the image pick-up surface of the vidicon 16 through the mirror 14 and the converging lens 15.

On the other hand, a beam of light emitted from the light source 20 enters the filter F which takes up only the infrared component from the beam. The infrared beam illuminates the indication plate 21. The beam emerging from the indication plate 21 is directed to the cornea Ec through half mirror 23, relay lenses 6 and 7, bored mirror 8 and objective lens 9. The beam impinging upon the cornea as a convergent beam is reflected upon the cornea toward the objective lens. The beam entering the objective lens as a slightly converged beam is focused completely by the objective lens 9 and thereafter it enters the bundle of optical fibers 24 through the bored mirror 8, relay lens 7 and half mirror 23. The beam coming out from the fiber bundle 24 is directed to enter the image pick-up surface of the vidicon 16 through the mirror 25, relay lens 26, half mirror 27, jump-up mirror 12, field lens 23 on which it is once converged, mirror 14 and pick-up lens 15.

Figure 3:
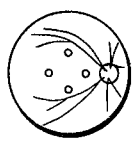
FIGS. 3 and 4 illustrate visual fields observed on the screen of a Braun tube.
Figure 4:
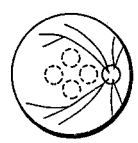

FIGS. 3 and 4 show examples of the visual field displayed on the Braun tube. When the spacing between the cornea Ec and the objective lens 9 is correct, the beam emerging from the indication plate 21 is converged accurately on the plane P and a clear and sharp image of the indication holes is formed also on the pick-up surface of the vidicon 16. On the contrary, if the spacing is incorrect and therefore the beam reflected upon the cornea Ec is not imaged precisely on the plane P, then there will be formed an obscure image of the indication holes on the pick-up surface of the vidicon 16. Thus, when a correct working distance is obtained, there is observed a clear and sharp image of the indication on the screen of the Braun tube as illustrated in FIG. 3 whereas when it is not obtained there is visible an obscure image of the indication as illustrated in FIG. 4.

The operator of the fundus camera adjusts the working distance while observing the image appearing on the screen of the Braun tube. The necessary adjustment can be made by slightly moving the fundus camera forward or backward to the position at which the image of the indication on the screen becomes clear and sharp. After bringing the photographing system (9, 10, 11) into focus to the fundus, the operator releases the shutter (not shown). Upon the time of releasing, the jump-up mirror 12 and the half mirror 27 are retracted and the movement of these mirrors to their retracted positions causes the strobo tube to flash so that an exposure of the film to the light is effected.

In the case of a fundus camera in which adjustment of focussing must be made while observing an image appearing on display means of decreased resolving power as compared with naked eyes, a method as proposed in U.S. Pat. No. 3,925,793 may be advantageously used. Namely, a beam for focussing is projected from an indication mark always conjugate with the film plane with respect to the fundus and the operator carries out focussing while observing the indication mark for focussing on display means. For focussing it is preferable to move the whole or a part of the imaging lens group 10 in the direction of the optical axis.

While description has been made of adjustment of spacing, adjustment of alignment also can be carried out with this embodiment. If alignment is not right and therefore there is some deviation between the center of the pupil of the eye E and the optical axis of the objective lens 9, the beam reflected upon the cornea will travel in a direction deviated from the normal direction. As a result, the image of the indication will not appear at a position predetermined therefore in the visual field. In such a case, the necessary correction of alignment can be made by moving the camera vertically and horizontally to the position at which the image of indication coincides with the predetermined position.

Figure 5:
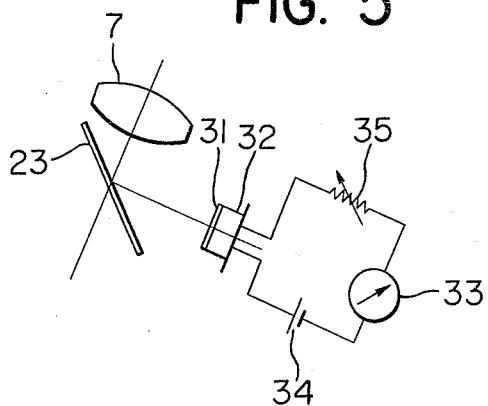
FIG. 5 is a partial view of a modification of the embodiment shown in FIG. 1.
Figure 6:
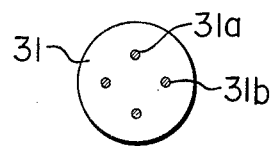
FIG. 6 is a plan of the mask plate used in the modification.

FIG. 5 shows a modification of the above described embodiment. At a position corresponding to the input end 24a of the optical fiber bundle 24 there is disposed a mask plate 31. The mask plate 31 has a plural number of light stopping points 31a, 31b . . . provided therein as illustrated in FIG. 6. Each stopping point is located at the position where an image of each indication hole is formed. The size of the stopping point is so measured that it is a little larger than the size of the image of the indication hole as formed when the working distance is right.

Designated by 32 is a photoelectric element which is, in this case, sensitive to light of the infrared range. This element 32 and an ampere-meter 33, a battery 34 and a variable resistor 35 together constitute a light metering and displaying circuit. Preferably, the indicator (ampere-meter) 33 is positioned in the vicinity of the Braun tube so that the dial of the indicator and the image of the fundus appearing on the Braun tube may be observed at the same time.

When this modification is employed, the mask 31 stops the beam for indication reflected upon the cornea so long as the working distance is correct. Therefore, there appears no output of the photoelectric element 32. But, if the working distance is incorrect, then the image of the indication formed on the mask 31 becomes obscure. Therefore, the beam is allowed to pass through the mask 31 around the stopping points 31a, 31b and so on and to enter the photoelectric element. Accordingly, the pointer of the ampere-meter 33 deviates. In such a case, the operator adjusts the position of the fundus camera by moving it forward or backward until the pointer indicates the zero point of the dial.

Figure 7:
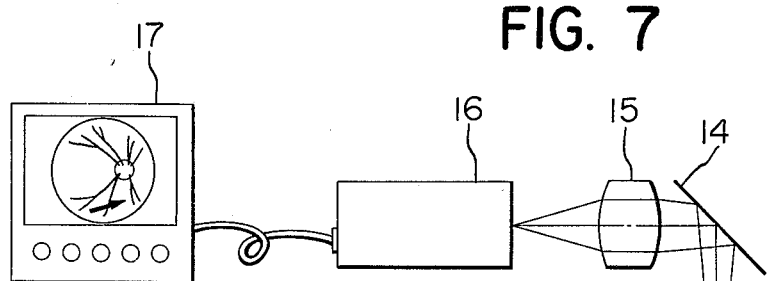
FIG. 7 schematically shows another embodiment of the invention.
Figure 7:
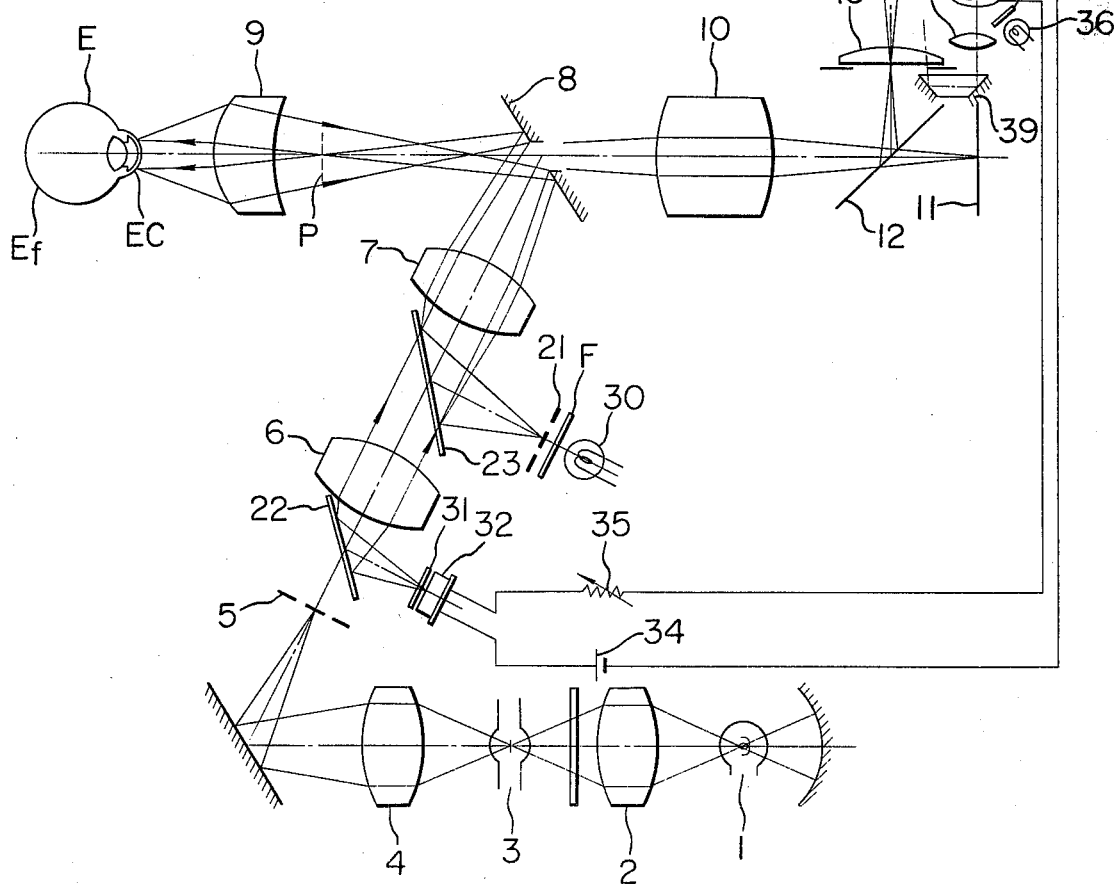

FIG. 7 shows another embodiment of the invention. In FIG. 7, the same elements as in FIG. 1 are designated by the same reference numerals and characters. This second embodiment is contrasted to the first embodiment of FIG. 1 in that the positions of the input and output of the indication beam are reversed as compared with the embodiment of FIG. 1 and that in the second embodiment, indication made by the pointer of an indicator appears on the screen of the Braun tube.

Designated by 30 is a tungsten lamp provided in place of luminescence diodes shown in FIG. 1. The reference numeral 36 designates a lamp for illuminating the ampere-meter 33 and 37 is an infrared filter. Designated by 38 is a projection lens the function of which is to form an image of the pointer of the indicator 33 on a plane conjugate with the film plane 11 with respect to the jump-up mirror 12. The reference numeral 39 designates a prism adapted for introducing the beam for display into the beam for forming the fundus image.

The manner of operation of the above described second embodiment is as follows:

The lamps 30 and 36 are put on. The beam emerged from the indication plate 21 is converged at first on the plane P through the half mirror 23, relay lens 7 and bored mirror 8. Thereafter, the beam is incident upon the cornea Ec in a state of a weakly diverged beam through the objective lens 9. The beam reflected upon the cornea is converged by the objective lens 9 and then imaged on the mask 31 through the bored mirror 8, relay lenses 7 and 6 and half mirror 31. If the working distance is right at that time, no beam of light is allowed to enter the photoelectric element 32 passing through the mask plate 31. But, when the working distance is incorrect, there occurs a deviation of the pointer of the indicator 33. Since the indicator 33 is illuminated with light of infrared range from the light source (36, 37), an image of the display dial of the indicator 33 is formed on the field lens by the action of the lens 38 and also by the action of the prism 39 which reflects the beam twice. As a result, on the pick-up surface of the vidicon 16 there are formed an image of the fundus and an image of the pointer at the same time, which are displayed on the screen of the Braun tube.

The operator adjusts the working distance while observing the images appearing on the screen. When the pointer indicates zero point of the dial, it means that the working distance has been correctly adjusted. After focussing, the operator can photograph the fundus.

Figure 8:
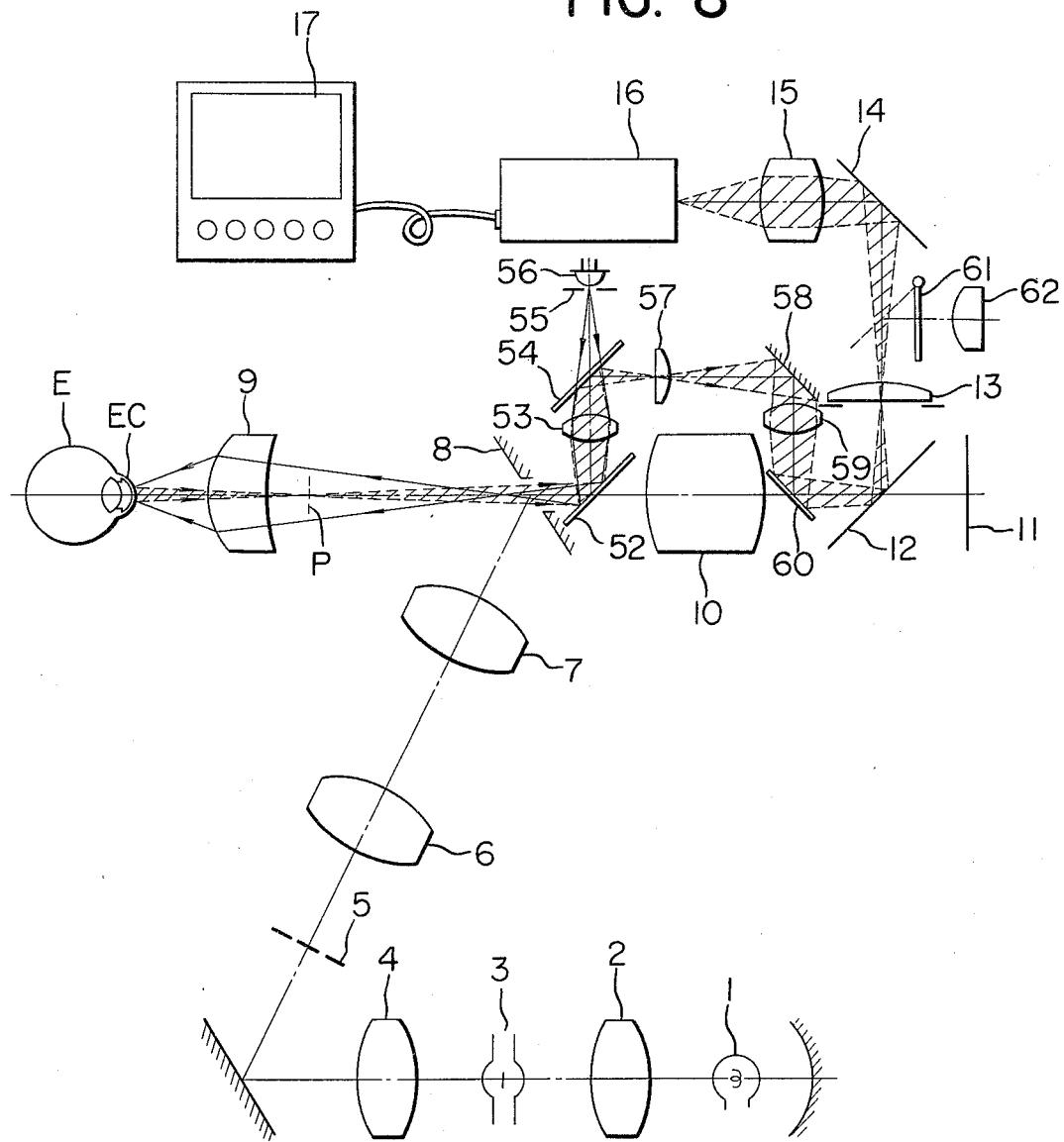
FIG. 8 schematically shows still a further embodiment of the invention.
Figure 9:
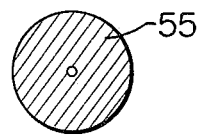
FIG. 9 is a plan of the indication plate used in the embodiment.

FIG. 8 shows a third embodiment of the invention. Elements 1–17 shown in FIG. 8 are identical with those shown in FIG. 1. But, as a vidicon there is used one that is sensitive to the visible range of light. 52 and 60 are half mirrors which are preferably so mounted that when a picture is taken, they may be retracted to positions outside of the effective light beam. 53 is a converging lens, 54 is a half mirror, 55 is an indication plate (FIG. 9), 56 is a luminescence diode and 57 is a field lens. The indication plate 55 and the plane P are conjugate with respect to the projection lens 53 and the half mirror 52. The beam from the plane P passes through the objective lens 9 and is reflected upon the cornea Ec. The reflected beam enters again the objective lens 9 now in the reversed direction. After passing through the objective lens 9, the beam is once converged and then it is again converged on the field lens 57 through the half mirror 52, projection lens 53 and half mirror 54.

Designated by 58 is a mirror for changing-over the light path and 59 is a relay lens. The relay lens 59 connects the image plane on the field lens 57 with the image plane on the field lens 13 in a conjugated relation.

Figure 10:
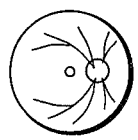
FIGS. 10 and 11 illustrate visual fields observed on the Braun tube of the embodiment shown in FIG. 8.
Figure 11:
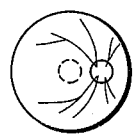

In the above described arrangement, a beam of light emitted from the luminescence diode 56 reflects upon the cornea. As a result, on the screen of the Braun tube there appears a sharp and clear or obscure image of indication. FIGS. 10 and 11 illustrate examples of the visual field on the Braun tube. When the image of indication appears obscure as illustrated in FIG. 11, the operator adjusts the position of the camera by moving it forward or backward to the position at which the indication image becomes clear and sharp.

Designated by 61 is a mirror obliquely mounted and 62 is an ocular lens 62. When the beam for forming an image of the fundus and the beam for indication reflected upon the cornea are directed to the ocular lens 62 by the mirror 61, observation with the naked eye becomes possible.

For the embodiment shown in FIGS. 1 and 8, adjustment of alignment is also possible. If there is any positional deviation in vertical or horizontal (right and left) direction between the optical axis of the objective lens and the eye, then the image of indication will appear at a position deviated from the normal position predetermined therefor. The operator can correct the deviation while observing the indication image appearing on the screen of the Braun tube so as to achieve a correct alignment.

While the invention has been particularly shown and described with reference to preferred embodiments thereof, it will be understood by those skilled in the art that the foregoing and other changes in forms and details can be made therein without departing from the spirit and scope of the invention.

What I claim is:

1. An eye examining instrument comprising:
   an eye examining system including objective optical means adapted to oppose an eye to be examined;
   an indication projection system for projecting at least one beam which does not form any image thereof on the surface of the eye and spaced from said objective optical means;
   an observation system for visibly detecting an image of the indication and receiving the light energy coming from the fundus of the eye to be inspected;
   an image transmitting system for transmitting the image of the indication and supplying the image of the indication to said observation system; and
   optical converging means for converging the beam reflected upon the cornea of the eye on an input surface of said image transmitting system,
   said optical converging means being disposed within said instrument such that the image projected by said indication projection system is sharply focused when the spacing between the instrument and the eye is correct, and blurred when said spacing is not correct.

2. An eye examining instrument as claimed in claim 1, wherein said indication projection system and said optical converging means have a common objective lens means, and said observation system comprises pick-up means connected to said eye examining system for detecting the image of the eye fundus, and an image display system electrically connected to said pick-up means.

3. An eye examining instrument as claimed in claim 1, wherein said image transmitting system comprises a bundle of fibers, an image focusing lens group for imaging the beams transmitted by said bundle of fibers.

4. An eye examining instrument as claimed in claim 1, wherein said eye examining system comprises, rear lens means disposed beyond said objective optical means, pick-up means for detecting the image surface of said rear lens means, and image display means operative with the output of said pick-up means, and wherein said observation system includes an image transmitting system for supplying an image formed by said optical converging means to said pick-up means.

5. An eye examining instrument as claimed in claim 4, wherein said optical converging means includes said front optical means.

6. An eye examining instrument as claimed in claim 1, wherein said eye examining system comprises a photographing system including said objective optical means, an illumination system for illuminating the fundus of the eye to be examined, and a photosensitive means, and said indication projection system projects said beam through said objective optical means, said optical converging means including said objective optical means, and wherein said observation system is connected with said eye examining system.

7. An eye examining instrument as claimed in claim 6, wherein said beam is an infrared beam and said observation system comprises an infrared image-fiber image converter.

8. An eye examining instrument comprising:
   an eye examining system including objective optical means adapted to be positioned opposite an eye to be examined and means for observing the eye to be examined:
   a mark projection system spaced from said objective optical means for projecting a beam which does not form any image thereof on the surface of the eye;
   masking means, provided with a detecting area, for defining the shape of the image of the mark on a masking plane;
   optical imaging means for imaging a beam reflected by the cornea of the eye on said masking plane; and
   photoelectric means, electrically connected to said photoelectric means, for providing said observation means with visible information,
   said masking means being positioned such that the image of the mark formed on said masking plane is sharply focused when the spacing between said instrument and the eye is correct, and is blurred when said spacing is not correct.

9. An eye examining instrument as claimed in claim 8, wherein said eye examining system comprises a photographing system including said objective optical means, an illumination system for illuminating the fundus of the eye to be examined and photosensitive means, and said mark projection system projects said beam through said objective optical means, and said optical imaging means includes said objective optical means.

* * * * *

UNITED STATES PATENT AND TRADEMARK OFFICE
CERTIFICATE OF CORRECTION

PATENT NO. : 4,251,139

DATED : February 17, 1981

INVENTOR(S) : ISAO MATSUMURA

It is certified that error appears in the above-identified patent and that said Letters Patent are hereby corrected as shown below:

Column 3, line 38, change "lengs" to --lens--.

Column 8, line 52, change "photoelectric" to --information--.

Signed and Sealed this

Twelfth Day of May 1981

[SEAL]

Attest:

RENE D. TEGTMEYER

Attesting Officer

Acting Commissioner of Patents and Trademarks